Figure 1:
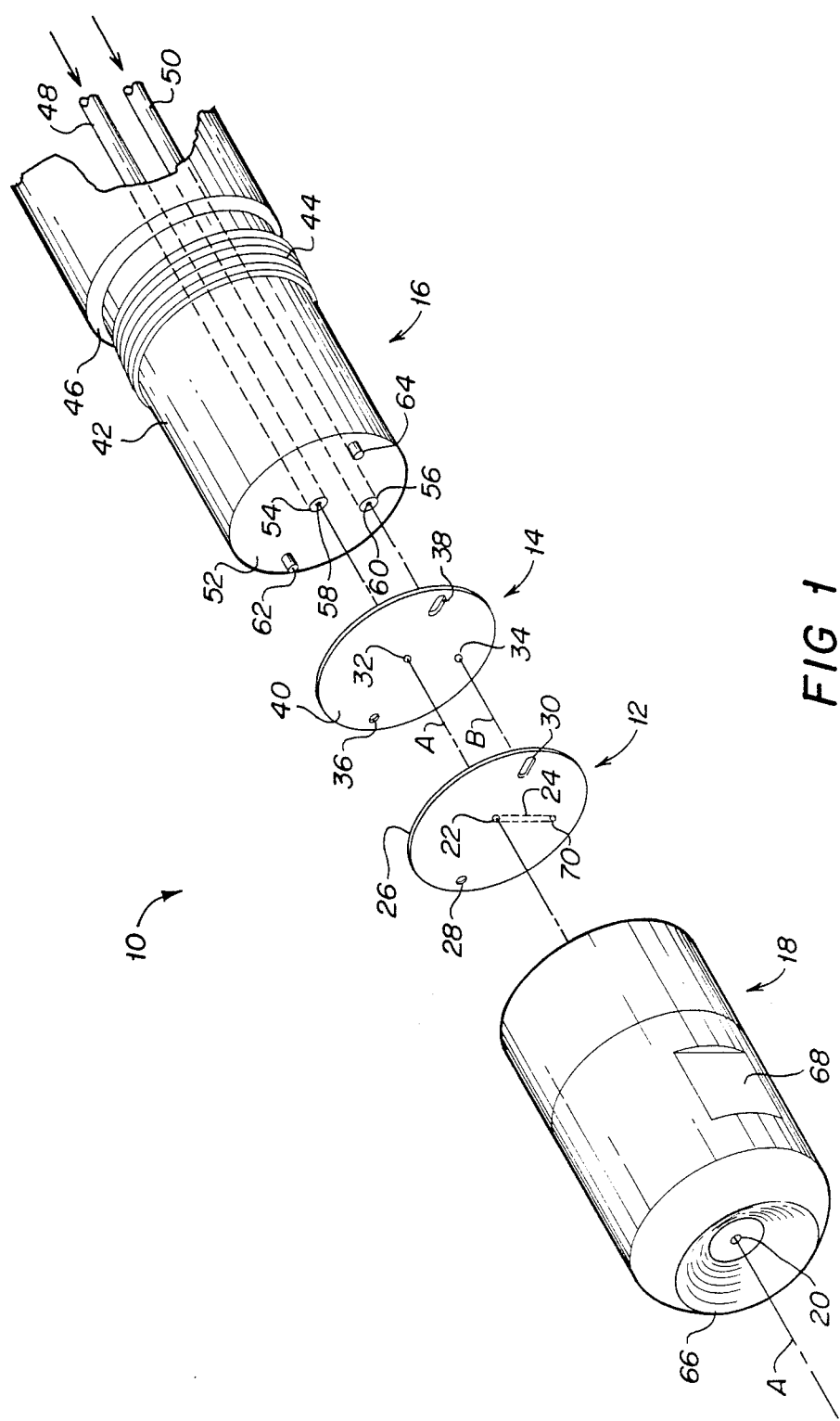

United States Patent [19]

Goodley et al.

[11] Patent Number: 4,746,068

[45] Date of Patent: May 24, 1988

[54] MICRO-NEBULIZER FOR ANALYTICAL INSTRUMENTS

[75] Inventors: Paul C. Goodley; Harvey D. Loucks, Jr., both of Cupertino

[73] Assignee: Hewlett-Packard Company, Palo Alto, Calif.

[21] Appl. No.: 924,709

[22] Filed: Oct. 29, 1986

[51] Int. Cl.$^4$ .............................................. B05B 7/10
[52] U.S. Cl. ..................................... 239/405; 239/429
[58] Field of Search ............... 239/405, 406, 418, 423, 239/424, 424.5, 426, 429, 434, 434.5, 403

[56] References Cited

U.S. PATENT DOCUMENTS

| | | | |
|---|---|---|---|
| 1,415,523 | 5/1922 | Cameron | 239/405 |
| 2,624,624 | 1/1953 | Kirschbaum | 239/403 |
| 4,018,387 | 4/1977 | Erb et al. | 239/405 |
| 4,261,511 | 4/1981 | Erb et al. | 239/434 |

Primary Examiner—Andres Kashnikow
Assistant Examiner—Karen B. Merritt
Attorney, Agent, or Firm—Paul L. Hickman

[57] ABSTRACT

A nebulizer assembly particularly well adapted as a liquid chromatograph/mass spectrometer interface including a pair of nebulizer plates, a base, and a cap for tightly holding the nebulizer plates against the base. A first nebulizer plate has a centrally located outlet orifice and a radially extending groove, and the second plate has a centrally located gas inlet orifice and a radially displaced liquid inlet orifice. The gas inlet orifice aligns with the outlet orifice and an aperture provided in the cap, and the liquid inlet orifice aligns with a section of the groove provided in the first nebulizer plate. When the gas inlet orifice is coupled to a pressurized gas source and the liquid inlet orifice is coupled to a pressurized liquid source, uniform droplets having a diameter of approximately 10 microns can be formed from an outlet orifice twice that diameter.

21 Claims, 2 Drawing Sheets

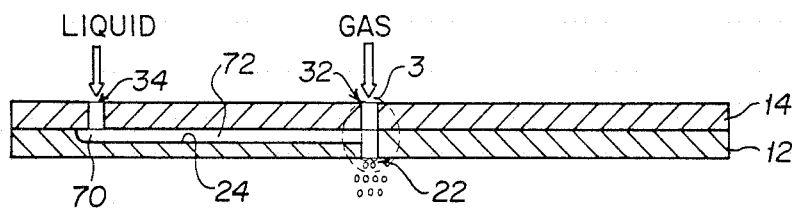
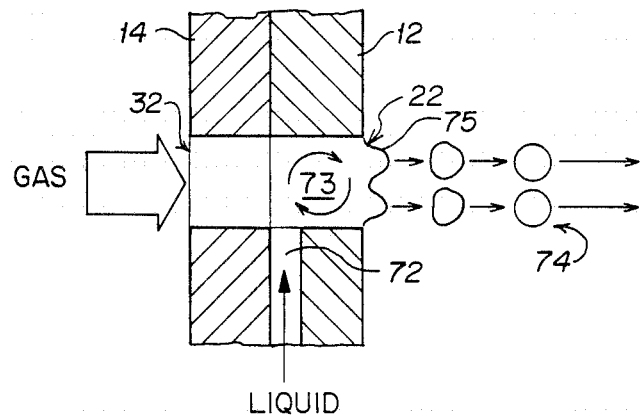
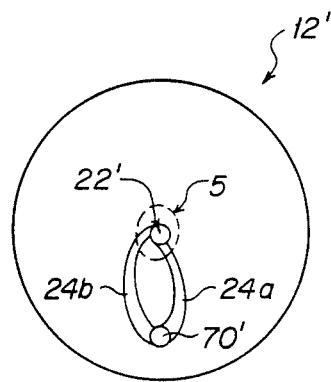
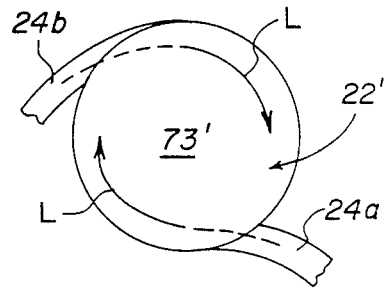

MICRO-NEBULIZER FOR ANALYTICAL INSTRUMENTS

BACKGROUND OF THE INVENTION

1. Field of the Invention

This invention relates generally to liquid sprayers, atomizers, and the like, and more particularly to nebulizers used in liquid chromatograph/mass spectrometers.

2. Description of the Prior Art

Some analytical instruments, such as the liquid chromatograph/mass spectrometer (LCMS), require the conversion of a liquid sample into a fine mist or spray. The liquid chromatograph portion of the LCMS machine separates organic compounds in a liquid sample, while the mass spectrometer portion of the LCMS machine identifies and quantifies the separated compounds. In order for the mass spectrometer portion of the instrument to function properly, the liquid samples containing the organic compounds must be converted into small, uniform droplets.

The device which creates the droplets in a LCMS machine is commonly known as a nebulizer. It has been an accepted fact in the industry that the droplet size produced by the nebulizer is approximately twice the size of the outlet orifice. In consequence, prior art nebulizers for LCMS instruments typically have an outlet orifice diameter of 5 microns and produce droplets approximately 10 microns in diameter.

The small outlet orifice of prior art nebulizer results in a number of problems. For one, prior art nebulizers orifices tend to become clogged by particulate matter or by diabatic freezing as the fluid is released from the nebulizer. Also, prior art nebulizers produce a broad range of droplet sizes which reduces the accuracy of the LCMS instrument. Furthermore, the small orifice size reduces the volume of droplets which can be produced.

Another problem with prior art nebulizers which may be related to their small outlet orifice size is that the nebulizers must be started at atmospheric pressure, and then pumped down to vacuum level pressures. This is apparently due to the fact that the high surface tension of the liquid across the small outlet orifices prevents initial droplet formation under vacuum conditions.

SUMMARY OF THE INVENTION

An object of this invention is to provide a nebulizer which produces uniformly sized droplets.

Another object of this invention is to provide a nebulizer of simple, low maintenance design, and one which is very resistant to clogging. A further object of this invention is to provide a nebulizer capable of delivering a high volume of droplets.

Yet another object of this invention is to provide a nebulizer which produces droplets smaller in diameter than its outlet orifice.

A still further object of this invention is to provide a nebulizer which may be started under vacuum conditions.

Briefly, the nebulizer includes a first disk provided with a centrally located outlet orifice, and a second disk having both a centrally located gas inlet orifice and a radially displaced liquid inlet orifice. A radial groove is provided in one of the two disks to couple the three orifices together and to form a turbulence volume at their juncture. When a pressurized gas is applied to the gas inlet orifice and a pressurized liquid is applied to the liquid inlet orifice, a turbulence is created in the turbulence volume which causes the ejection of uniform droplets which are smaller in size than the outlet orifice. As a consequence, the outlet orifice diameter can be increased.

An advantage of the present invention is that the nebulizer produces extremely uniform droplet sizes.

Another advantage of this invention is that the nebulizer can be quickly disassembled for inspection and repair, and is very resistant to clogging due to its large outlet orifice size.

Yet another advantage of this invention is that it produces droplets smaller in diameter than its outlet orifice.

A further advantage of this invention is that it is capable of producing a high volume of droplets due to its large orifice size.

A still further object of this invention is that it may be started under vacuum conditions.

These and other objects and advantages of the present invention will be apparent to those skilled in the art after reading the following descriptions and studying the various figures of the drawing.

BRIEF DESCRIPTION OF THE DRAWINGS

FIG. 1 is an exploded, perspective view of a nebulizer assembly in accordance with the present invention;

FIG. 2 is a cross-sectional view taken through the two nebulizer plates after they have been assembled;

FIG. 3 is an enlarged view of the portion of FIG. 2 that is encircled by broken line 3;

FIG. 4 is a plan view of an alternate embodiment for a nebulizer plate in accordance with an alternate embodiment of the present invention; and FIG. 5 is an enlarged view of the portion of FIG. 4 that is encircled by broken line 5.

DETAILED DESCRIPTION OF THE PREFERRED EMBODIMENT(S)

Referring to FIG. 1, a nebulizer assembly 10 in accordance with the present invention includes a nebulizer plate 12, a nebulizer plate 14, a base 16, and a hollow cap 18 having a cap aperture 20. When assembled, a fine mist or spray emanates from cap aperture 20 to provide uniformly sized droplets for analytical machine such as liquid chromatograph/mass spectrometers (LCMS).

Nebulizer plates 12 and 14 are thin, disk shaped members, and are preferably made from a durable, non-reactive material such as stainless steel. Nebulizer plate 12 is provided with an outlet orifice 22 and, as indicated by broken lines, a groove 24, which is formed on an abutment surface 26. The outlet orifice 22 is preferably 15 microns to 150 microns in diameter, and is typically 20 microns in diameter to produce uniform 10 micron droplets. The nebulizer plate 12 is also provided with an alignment hole 28 and an alignment slot 30.

Nebulizer plate 14 is provided with a gas inlet orifice 32, a liquid inlet orifice 34, an alignment hole 36, and an alignment slot 38. An abutment surface 40 of nebulizer plate 14 is adapted to tightly abut against abutment surface 26 of nebulizer plate 12.

Base 16 includes a cylindrical member 42 provided with threads 44 and a shoulder 46. The cylindrical member 42 is provided with bores that are receptive to a gas conduit 48 and a liquid conduit 50. The gas conduit 48 is coupled to a pressurized gas source, and the liquid conduit 50 is coupled to a pressurized liquid source, such as an output of the liquid chromatograph of an LCMS instrument.

The base 16 has a base surface 52 provided with large holes 54 and 56 which are receptive to the ends of conduits 48 and 50, respectively. The ends of the conduits 48 and 50 are flush with and form a part of the base surface 52. The openings of conduits 48 and 50 comprise a gas outlet 58 and a liquid outlet 60 at the base surface 52.

Extending outwardly from base surface 52 are a pair of alignment pins 62 and 64. Alignment pin 62 is adapted to extend through alignment holes 36 and 28 of plates 14 and 12, respectively, and alignment pin 64 is adapted to extend through alignment slots 38 and 30 of plates 14 and 12, respectively.

Cap 18 is an elongated, hollow, cylindrical member having a concave, conical forward end 66 having the cap aperture 20 at its inverted apex. A wrench groove 68 and a corresponding wrench groove on the other side of cap 18 (not shown) provide a means for tightening the cap 18. A set of internal threads (not shown) of cap 18 are adapted to engage with threads 44 of base 16.

To assemble the nebulizer assembly 10 of FIG. 1, plate 14 is placed against base surface 52 such that pin 62 engages alignment hole 36 and pin 64 engages alignment slot 38. Then, plate 12 is placed against plate 14 such that pin 62 engages alignment hole 28 and pin 64 engages alignment slot 30. Next, the cap 18 is placed over the plates 12 and 14, and is screwed onto base 16. A crescent or box-end wrench can be used to firmly tighten the cap 18 onto the base 16.

When assembled as described above, the abutment surfaces 26 and 40 of plates 12 and 14, respectively, are tightly pressed together and, in fact, form a gas and liquid-tight seal where they contact. Also, the plate 14 tightly seals against base surface 52, and the plate 12 tightly seals against a surface within cap 18 (not shown).

The nebulizer assembly 10, the gas outlet 58, gas inlet orifice 32, outlet orifice 22, and cap aperture 20 are all aligned along a central axis A. The liquid outlet 60, liquid inlet orifice 34, and a section 70 of groove 24 are similarly aligned along an axis B. Gas may therefore flow out of gas outlet 58, through gas inlet orifice 34, through outlet orifice 22, and out of the cap aperture 20. Liquid may flow out of liquid orifice 60, through liquid inlet orifice 34, into channel 24, through outlet orifice 22, and out of cap aperture 20. The tight, compressive fit between the abutting surfaces of plates 12 and 14, between plate 14 and base surface 52, and between plate 12 and cap 18 prevents fluid leakage.

The operation of the nebulizer plates 12 and 14 will be discussed in greater detail with reference to FIGS. 2 and 3. As seen in FIG. 2, the plates 12 and 14 are tightly pressed together such that gas inlet orifice 32 is aligned with outlet orifice 22, and such that liquid inlet orifice 34 is aligned with a portion 70 of groove 24. When the plates 12 and 14 are tightly pressed together, the groove 24 forms a channel 72 along which liquid may flow from liquid inlet orifice 34 to join with gas from the gas inlet orifice 32 at a turbulence volume 73. It should be noted that the groove can equally well be provided in the plate 14, or could be provided in both plates 14 and 12.

Referring now to FIG. 3, the gas enters gas inlet orifice 32 as indicated by the arrow. The liquid travelling through channel 72 enters the turbulence volume 73 substantially radially and causes a churning and shearing action of the liquid proximate to outlet orifice 22. This churning and shearing is possible due to the relatively large size of the outlet orifice, which reduces the surface tension of the liquid across its opening. In other words, a film of liquid 75 formed across the opening of outlet orifice 22 is stretched far enough that the gas pressure can break its surface tension, as opposed to prior art nebulizer with small diameter outlet orifices. The churning, tearing, and shearing produces uniformly sized droplets approximately one-half the diameter of the outlet orifice 22, with a droplet size deviation of less than 10%.

With reference to FIGS. 4 and 5, an alternate embodiment for a nebulizer plate 12' includes a pair of grooves 24a and 24b coupling a section 70' to an outlet orifice 22'. As seen in the enlarged, detailed view of FIG. 5, the grooves 24a and 24b serve as channels which release liquid L in a tangential fashion into a turbulence volume 73' relative to the axis A of outlet orifice 22', as opposed to the radial fashion described previously. This causes the liquid L to swirl in a vortex and aids in the shearing and churning processes which form uniformly sized droplets that are smaller in diameter than the size of the outlet orifice 22'.

While this invention has been described with reference to several preferred embodiments, it is contemplated that various alterations and permutations of the invention will become apparent to those skilled in the art upon a reading of the preceding descriptions and a study of the drawing. It is therefore intended that the scope of the present invention be determined by the following appended claims.

What is claimed is:

1. A nebulizer comprising:
   a first member having a first abutment surface, said first member being provided with an outlet orifice extending through said first member and opening on said first abutment surface;
   a second member having a second abutment surface, said second member being provided with a gas inlet orifice and a liquid inlet orifice extending through said second member and opening on said second abutment surface, where said first abutment surface is juxtaposed with said second abutment surface such that said outlet orifice and said gas inlet orifices are substantially aligned; and
   groove means coupling said liquid inlet orifice to said substantially aligned outlet orifice and gas inlet orifice, said groove means being provided in at least one of said first abutment surface and said second abutment surface, said groove means opening tangentially upon said substantially aligned outlet orifice and gas inlet orifice;
   whereby fluid may flow from said gas inlet orifice and said liquid orifice to said outlet orifice, where gas flowing out of said groove means and tangentially into said substantially aligned outlet orifice and gas inlet orifice creates a swirling vortex therein.

2. A nebulizer as recited in claim 1 wherein said first member includes a first plate, and wherein said second member includes a second plate.

3. A nebulizer recited in claim 1 wherein said groove means is provided in said first abutment surface.

4. A nebulizer as recited in claim 3 wherein said groove means provided in said first abutment surface is a first groove means, and further comprising second groove means provided in said second abutment surface.

5. A nebulizer as recited in claim 4 wherein said first groove means and said second groove means are in substantial alignment.

6. A nebulizer as recited in claim 1 wherein said groove means is provided in said second abutment surface.

7. A nebulizer as recited in claim 1 wherein said groove means includes a pair of grooves, each opening at said output orifice and said gas inlet orifice from opposing directions.

8. A nebulizer as recited in claim 2 further comprising holding means for holding said first abutment surface against said second abutment surface.

9. A nebulizer as recited in claim 8 wherein said holding means includes a base means and cap means provided with a cap aperture, said cap means being removably engagable with said base means and receptive to said first plate and said second plate, such that said first plate and said second plate may be compressed between said base means and said cap means with said outlet orifice being aligned with said cap aperture.

10. A nebulizer as recited in claim 9 wherein said base means includes a base surface receptive to said second plate, and a gas outlet and a liquid outlet aligned with said gas inlet orifice and said liquid inlet orifice, respectively.

11. A nebulizer as recited in claim 10 further comprising gas conduit means adapted to couple said gas outlet to a pressurized gas source, and liquid conduit means adapted to couple said liquid outlet to a pressurized liquid source.

12. A nebulizer as recited in claim 10 further comprising first alignment means coupled to said base surface, and wherein said first plate and said second plate are provided with second alignment means adapted to mate with said first alignment means.

13. A nebulizer as recited in claim 12 wherein said first alignment means includes at least one alignment pin, and wherein said second alignment means includes at least one alignment hole through both said first plate and said second plate.

14. A nebulizer as recited in claim 1 wherein the droplets produced by said nebulizer are smaller in diameter than said outlet orifice.

15. A nebulizer as recited in claim 14 wherein said diameter of said outlet orifice is between 15 and 150 microns.

16. A nebulizer comprising:
a first plate having a first abutment surface, said first plate being provided with an outlet orifice extending through said first plate from said first abutment surface, said outlet orifice having a lateral dimension between 15 and 150 microns;
a second plate having a second abutment surface, said second plate being provided with a gas inlet orifice and a liquid inlet orifice extending through said second plate from said second abutment surface, where said first abutment surface is juxtaposed with said second abutment surface with said outlet orifice and said gas inlet orifice in substantial alignment; and channel means disposed between said first abutment surface and said second abutment surface coupling said liquid inlet orifice to said outlet orifice and said gas inlet orifice;
whereby droplets produced by said nebulizer are smaller in diameter than said outlet orifice.

17. A nebulizer as recited in claim 16 wherein said channel means comprises groove means provided in at least one of said first abutment surface and said second abutment surface.

18. a nebulizer as recited in claim 16 wherein said channel means opens substantially radially on said outlet orifice and gas inlet orifice.

19. A nebulizer as recited in claim 16 wherein said channel means opens substantially tangentially on said outlet orifice and said gas inlet orifice.

20. A nebulizer as recited in claim 16 further comprising holding means including a base means and a cap means, said cap means being provided with a cap aperture, said cap means being removably engagable with said base means and receptive to said first plate and said second plate, such that said first plate and said second plate may be compressed between said base means and said cap means with said outlet orifice being aligned with said cap aperture.

21. A nebulizer as recited in claim 20 further comprising first alignment means coupled to said base surface, and wherein said first plate and said second plate are provided with second alignment means adapted to mate with said first alignment means.

* * * * *